United States Patent [19]  
Takaishi et al.

[11] Patent Number: 4,533,770  
[45] Date of Patent: Aug. 6, 1985

[54] 2-EXO-HYDROXY-ENDO-TRICYCLO[6.2.1.0²,⁷]UNDECANE

[75] Inventors: Naotake Takaishi, Utsunomiya; Hitoshi Takahashi, Ichikaimachi; Yoshiaki Inamoto, Utsunomiya, all of Japan

[73] Assignee: Kao Corporation, Tokyo, Japan

[21] Appl. No.: 627,553

[22] Filed: Jul. 3, 1984

[30] Foreign Application Priority Data

Jul. 15, 1983 [JP] Japan .................... 58-129233

[51] Int. Cl.³ ............................. C07C 35/22
[52] U.S. Cl. ................................... 568/817
[58] Field of Search ......................... 568/817

[56] References Cited

U.S. PATENT DOCUMENTS 4,036,892 7/1977 Inamoto et al. ............... 568/817  
4,036,893 7/1977 Inamoto et al. ............... 568/817  
4,087,467 5/1978 Inamoto et al. ............... 568/817

FOREIGN PATENT DOCUMENTS 24329 8/1970 Japan ......................... 568/817

OTHER PUBLICATIONS

Swithenbank et al., "J. Chem. Soc." p. 4573 (1963).

Takaishi et al., "Synthesis" (1983), p. 293.

Primary Examiner—Werren B. Lone  
Attorney, Agent, or Firm—Oblon, Fisher, Spivak, McClelland & Maier

[57] ABSTRACT

Disclosed is 2-exo-hydroxy-endo-tricyclo[6.2.1.0²,⁷]undecane represented by the following formula (I):

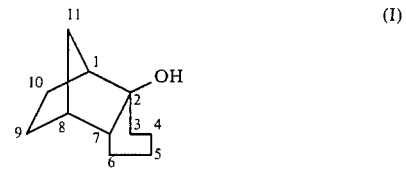

The tricycloundecanol of the formula (I) has green, camphor-like and woody odor and is useful as an aroma chemical. Furthermore, owing to the aliphatic polycyclic structure like adamantyl alcohol, it is expected to have antiviral, antimicroviral and plant hormone activities.

The tricycloundecanol (I) of the invention is prepared by subjecting endo-tricyclo[6.2.1.0²,⁷]undecane to hydroxylation at the bridgehead position with a substituted perbenzoic acid.

1 Claim, No Drawings

2-EXO-HYDROXY-ENDO-TRICYCLO[6.2.1.0$^{2,7}$]UNDECANE

BACKGROUND OF THE INVENTION

This invention relates to a novel tricycloundecanol and, more particularly, to 2-exohydroxy-endo-tricyclo[6.2.1.0$^{2,7}$]undecane represented by the following formula (I):

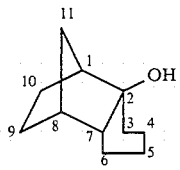

The tricycloundecanol of the formula (I) according to the invention has a green, camphor-like and woody odor, reminiscent of a component of patchouli oil and is useful as an aroma chemical. Furthermore, since it has an aliphatic polycyclic structure like naturally occurring sesquiterpene alcohols and synthetic tricyclic aliphatic alcohols such as adamantyl alcohol, it is expected to have various physiological activities owned by said alcohols, namely antiviral, antimicrobial and plant hormone activities, among others.

DETAILED DESCRIPTION OF THE INVENTION AND PREFERRED EMBODIMENTS

The tricycloundecanol (I) according to the invention is produced, for example, by subjecting endo-tricyclo[6.2.1.0$^{2,7}$]undecane (II) to hydroxylation at the bridgehead position (the present inventors, Synthesis, 1983, 293) with a substituted perbenzoic acid, such as m-chloroperbenzoic acid, in accordance with the following reaction equation:

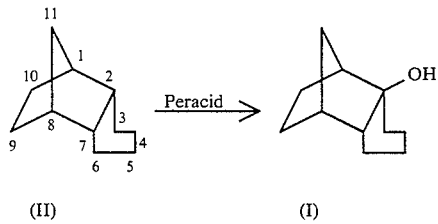

Thus, for instance, the reaction is suitably carried out by heating under reflux the starting material endo-tricyclo[6.2.1.0$^{2,7}$]undecane (II) and 1 to 10 moles, per mole of (II), of a peracid in a halogenated hydrocarbon solvent, such as chloroform, methylene chloride or carbon tetrachloride, or in an aromatic hydrocarbon solvent, such as benzene, toluene or xylene, or in some other appropriate solvent for 5 to 40 hours.

The starting material for practising the invention, the tricycloundecane (II), can be synthesized, for example, by hydrogenating 3,6-dioxoendo-tricyclo[6.2.1.0$^{2,7}$]undeca-4,9-diene (III), which is obtainable by the Diels-Alder reaction between cyclopentadiene and parabenzoquinone, and then subjecting the hydrogenation product to the Wolff-Kishner reduction [C. Swithenbank et al., J. Chem. Soc., 4573 (1963)] in accordance with the following reaction scheme:

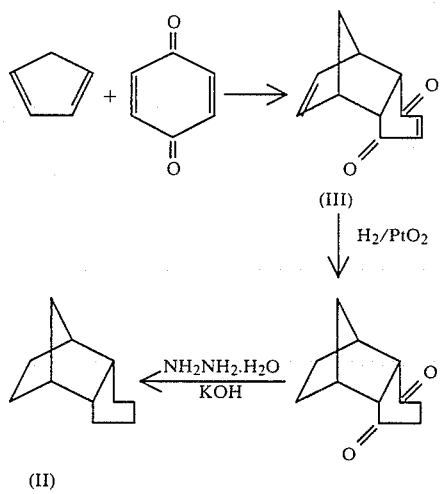

The following examples illustrate the invention.

EXAMPLE 1

A mixture of 1.50 (10 mmol) of endo-tricyclo[6.2.1.0$^{2,7}$]undecane, 1.73 g (10 mmol) of m-chloroperbenzoic acid and 15 ml of 1,2-dichloroethane is heated with stirring at 65° C. (bath temperature) for 24 hours. After cooling, 50 ml of 1,2-dichloroethane is added, and the whole mixture is washed twice with two 15-ml portions of 1N aqueous sodium hydroxide and then with water, dried over anhydrous sodium sulfate, and concentrated. The concentrate is subjected to silica gel column chromatography. After removal of unreacted tricycloundecane by elution with n-hexane, elution is carried out with n-hexane-chloroform (3:1) and 0.66 g (39.5% yield) of 2-exo-hydroxy-endo-tricyclo[6.2.1.0$^{2,7}$]undecane is recovered from the eluate. This product has a strong camphor-like odor.

Melting point: 52.5°–53° C.
Boiling point: 70° C./1 mm Hg.
Elementary analysis:
Calculated for $C_{11}H_{18}O$: C, 79.5%; H, 10.9%; Found: C, 79.6%; H, 11.0%;
IR (KBr, cm$^{-1}$): 3350, 2950, 2875, 2850, 1480, 1460, 1370, 1320, 1295, 1260, 1235, 1220, 1175, 1125, 1080, 1065, 1030, 995, 980, 955, 930, 920, 885, 825.
$^1$H-NMR (solvent: CDCl$_3$; internal standard: TMS; δ): 0.9–2.3 (complicated multiplet, 17H) 1.7 (s, 1H, —OH).
$^{13}$C-NMR (solvent: CDCl$_3$; internal standard: TMS; δc): 16.0(t), 19.5(t), 21.0(t), 21.2(t), 24.2(t), 26.9(t), 36.5(t), 40.4(d), 49.2(d), 51.5(d), 78.4(s).
MS (m/e, relative intensity) 166(M$^+$,1), 148(13), 120(33), 98(100), 92(21), 91(29), 79(19), 70(15), 67(22), 41(20).

EXAMPLE 2

| Lavender cologne: | % by weight |
|---|---|
| Lavender oil | 100 |
| Lavender absolute | 15 |
| Bergamot oil | 70 |
| Lemon oil | 200 |
| Orange oil | 10 |
| Verbena oil | 30 |
| Eugenol | 25 |
| Rose Brugarian oil | 5 |

| -continued | |
|---|---|
| Lavender cologne: | % by weight |
| Jasmine absolute | 30 |
| Rhodinol | 30 |
| alpha-Hexylcinnamic aldehyde | 100 |
| Oakmoss absolute | 10 |
| Vetiver oil | 10 |
| Patchouli oil | 20 |
| Musk ketone | 70 |
| Mugnet base | 140 |
| Rose base | 50 |
| Terpinyl acetate | 40 |
| Labdanum oil | 20 |
| | 975 |

It was noted that addition of 25 parts by weight of 2-exo-hydroxy-endo-tricyclo[6.2.1.0$^{2,7}$]-undecane according to the invention to the above lavender cologne results in markedly increased greenness and freshness.

Furthermore, the compound according to the invention is very useful in preparing perfumes of the lavandin, bergamot, fougere and chypre types as well as the lavender type.

What is claimed is:

1. 2-Exo-hydroxy-endo-tricyclo[6.2.1.0$^{2,7}$]undecane represented by the following formula (I):

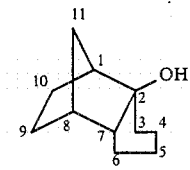

* * * * *